United States Patent [19]

Nelson et al.

[11] Patent Number: 5,248,766

[45] Date of Patent: Sep. 28, 1993

[54] OXIRANE-MODIFIED HEMOGLOBIN BASED COMPOSITION

[75] Inventors: Deanna J. Nelson, Libertyville; Ton T. Hai, Lake Villa; Ana Srnak, Skokie, all of Ill.

[73] Assignee: Baxter International Inc., Deerfield, Ill.

[21] Appl. No.: 873,524

[22] Filed: Apr. 21, 1992

Related U.S. Application Data

[63] Continuation of Ser. No. 569,316, Aug. 17, 1990, abandoned.

[51] Int. Cl.$^5$ .......................... C07K 3/08; C07K 13/00
[52] U.S. Cl. ..................................... 530/385
[58] Field of Search ........................... 530/385; 514/6

[56] References Cited

U.S. PATENT DOCUMENTS

| | | | |
|---|---|---|---|
| 3,925,344 | 12/1975 | Mazur | 530/385 |
| 4,001,200 | 1/1977 | Bonsen et al. | 530/385 |
| 4,001,401 | 1/1977 | Bonsen et al. | 530/385 |
| 4,053,590 | 10/1977 | Bonsen et al. | 530/385 |
| 4,061,736 | 12/1977 | Morris et al. | 530/385 |
| 4,179,337 | 12/1979 | Davis et al. | 435/181 |
| 4,301,144 | 11/1981 | Iwashita et al. | 530/385 |
| 4,336,248 | 6/1982 | Bonhard et al. | 530/385 |
| 4,377,512 | 3/1983 | Ajisaka et al. | 530/385 |
| 4,412,989 | 11/1983 | Iwashita et al. | 530/385 |
| 4,473,496 | 9/1984 | Scannon | 530/385 |
| 4,529,719 | 7/1985 | Tye | 530/385 |
| 4,584,130 | 4/1986 | Bucci et al. | 530/385 |
| 4,598,064 | 7/1986 | Walder | 530/385 |
| 4,600,531 | 7/1986 | Walder | 530/385 |
| 4,670,417 | 6/1987 | Iwasaki et al. | 530/385 |
| 4,806,595 | 2/1989 | Noishiki et al. | 525/54.2 |
| 4,857,636 | 8/1989 | Hsia | 530/385 |
| 4,900,816 | 2/1990 | Wong | 530/385 |
| 4,920,194 | 4/1990 | Feller et al. | 530/385 |

FOREIGN PATENT DOCUMENTS 0361719 4/1990 European Pat. Off. .
0361720 4/1990 European Pat. Off. .
2616086 4/1976 Fed. Rep. of Germany .

OTHER PUBLICATIONS

Ajinomoto Co., *Hemoglobin-Polyalkylene Glycol Complexes as Blood Substitutes*, Pharmaceuticals 101:157714n, 1984.

Ajinomoto Co., *Polyalkylene Glycol-Bound Hemoblogins as Blood Substitutes*, Pharmaceuticals 101:1982390v, 1984.

Dellacherie, E. et al., *Chemically Modified Hemoglobins as Oxygen Carriers*, Pharmaceuticals 103: 109915y, 1985.

Dellacherie, E. et al., *Soluble Polymers as Hemoglobin Carriers in Blood Substitutes*, Makromol. Chem. Suppl. 9:43-56, 1985.

Iwasaki, et al., *Preparation of Hemoglobin-Polykylene Glycol Complexes as Blood Substitutes*, Pharmaceuticals vol. 105:12188s, 1986.

Leonard, Michele et al., *Acylation of Human Hemoglobin With Polyoxyethylene Derivatives*, Biochimica et Biophysica Acta. 791:219-225, 1984.

Leonard, M. et al., *Synthesis of Monomethoxylpolyoxyethylene-bound Haemoglobins*, Tetrahedron 40:1581-1584, 1984.

Marks, D. et al., *Antibody Response to Transfusion With Pyridoxalated Polymerized Hemoglobin Solution*, Military Med. 152:473-477, 1987.

Mok, D. et al., *Cross-Linked Hemoglobins as Potential Plasma Extenders* Federation Proceedings, v. 34:q459-1460, 1975.

*Primary Examiner*—Robert A. Wax
*Assistant Examiner*—Richard C. Ekstrom
*Attorney, Agent, or Firm*—Sarah E. Bates; Bradford R. L. Price; Susan Bennett Fentress

[57] ABSTRACT

A non-immunogenic mixture of hemoglobin based modified monomers and oligomers produced by the polymerization of a hemoglobin based solution in the presence of a three membered heterocyclic ring, i.e. polyether oxirane. The modified hemoglobin composition has a $P_{50}$ of at least equivalent to the $P_{50}$ of human red blood cell hemoglobin.

3 Claims, 7 Drawing Sheets

□ LACTATED RINGER'S  △ POLYETHER OXIRANE-
POLYMERIZED HEMOGLOBIN

□ LACTATED RINGER'S △ POLYMERIZED HEMOGLOBIN

OXIRANE-MODIFIED HEMOGLOBIN BASED COMPOSITION

This is a continuation, of application Ser. No. 7/569,316, filed on Aug. 17, 1990, now abandoned.

BACKGROUND OF THE INVENTION

1. Field of the Invention

This invention relates to a hemoglobin based composition and the method to make the same. In particular, it relates to a method for crosslinking a hemoglobin based solution to create a hemoglobin based composition which has the capacity to transport oxygen for an increased length of time, while still retaining at least the oxygen affinity of hemoglobin in human red cells.

2. Description of the Prior Art

In current medical practice, when it is necessary to infuse patients who have experienced blood loss, such as trauma victims or surgical patients, with oxygen-carrying materials, only whole blood or packed, red blood cells are used. It is necessary to carefully match the donor and the recipient blood type; testing which can delay the blood infusion. As a result, patients suffering substantial blood loss are subjected to periods of oxygen deprivation which is detrimental. Furthermore, even when autologous, patient-donated, red blood cells are available through previous phlebotomy and storage, the oxygen-carrying capacity and safety of these autologous cells has declined as a consequence of the storage. As a result, for a period of as much as 24 hours after transfusion, the patient may be subject to sub-optimal oxygen delivery. Finally, there is the ever-present danger to the patient of viral and/or bacterial contamination in all transfusions of whole blood and red cells derived from it.

Thus, there is a recognized need for a substance that is useful for oxygen carriage and delivery under normal environmental conditions and that incorporates the following features. Ideally, the substance shall carry and deliver oxygen to devices, organs and tissues such that normal oxygen tensions may be maintained in these environments. The substance shall be non-antigenic and non-pyrogenic (i.e. less than 0.25 EU/mL). The substance shall be free of bacterial and/or viral contamination. The substance shall be safe and non-toxic. The substance shall be miscible with blood and serum. The substance shall have viscosity, colloid and oncotic properties comparable to blood. It is desirable to have a substance that will be retained in the vascular system of the patient for a long period of time, since this will permit erythropoeisis and maturation of the patient's own red cells. Furthermore, the substance shall not interfere with or hinder erythropoeisis.

It has been recognized that the natural, mammalian protein for oxygen-carriage and -delivery, hemoglobin, can be separated from the red blood cell wall membranes or stroma which contain the specific antigens that determine blood type and from other cell and plasma components. If such separation and isolation is effected, the resulting stroma-free hemoglobin contains no antigenic materials; thus, blood typing and matching are no longer necessary. For example, a typical preparation of stroma-free hemoglobin involves washing red blood cells to remove residual plasma and cell debris, lysing the red cells to release hemoglobin, and filtering and ultrafiltering the hemoglobin to separate it from contaminants. K. Bonhard, B. Eichentopf, and N. Kothe, "Process for Obtaining Hepatitis-Safe, Sterile Hemoglobin Solutions Free of Pyrogens and Stroma," U.S. Pat. No. 4,439,357, N. Kothe and B. Eichentopf, "Method of Preparing Highly Purified, Stroma-Free, Non-Hepatitic Human-Animal Hemoglobin Solutions, U.S. Pat. No. 4,526,715. The process for isolating and purifying the stroma-free hemoglobin incorporates process steps to eliminate bacterial and viral contamination. U.S. Pat. Nos. 4,598,064 and 4,600,531 (hereby incorporated by reference).

However, stroma-free hemoglobin does not meet the substance-suitability criteria defined above. For example, although it is known that stroma-free hemoglobin is capable of carrying oxygen (S. F. Rabiner et al., J. Exp. Med., Vol. 126, p. 1142, 1967.), in the absence of specific additional substances known as effectors, stroma-free hemoglobin has too high an affinity for oxygen to be useful. As a result, stroma-free hemoglobin cannot maintain normal oxygen tensions in organs and tissues. Furthermore, in its natural form, stroma-free hemoglobin is a tetrameric aggregate (molecular weight 64,500) made up of a pair of dimer-aggregates (molecular weight 32,250), each of which consists of one alpha-protein chain and one beta-protein chain. The dimer-aggregates are not held together by any covalent bond. Following infusion of stroma-free hemoglobin, this protein naturally breaks down into these pairs of dimer-aggregates, which do not deliver oxygen. The dimers are sufficiently small to be removed by filtration through the kidney and excreted in the urine. Studies have shown that the retention half-life of stroma-free hemoglobin or its breakdown dimers in the circulation is approximately two hours, i.e., the concentration is reduced by one-half every two hours. This period is far shorter than the time required for regeneration and maturation of the red blood cells in the bone marrow. Thus, stroma-free hemoglobin becomes increasingly ineffective with the passage of time. Moreover, the stroma-free hemoglobin breakdown is so rapid that the dimers accumulate in the kidney and other organs and cause damage to these organs. As a consequence, stroma-free hemoglobin may lack the clinical safety that is required of an oxygen-carrying substance. S. L. Baker and E. C. Dodds, *Brit. J. Exp. Pathol.* 6: 247, 1925. Taken together, all of the findings indicate that without crosslinking, tetrameric hemoglobin is unsuitable as a vehicle for a long-term delivery of oxygen to the tissue.

A number of modified hemoglobins that address some of the shortcomings of stroma-free hemoglobin are recognized. The known modification methods include various means for intramolecular crosslinking of stroma-free hemoglobin; for intermolecular crosslinking of stroma-free hemoglobin with low-molecular weight agents; for intra- and intermolecular crosslinking of stroma-free hemoglobin with low molecular weight agents; and for coupling of stroma-free hemoglobin to other polymers.

Methods for intramolecular crosslinking of stroma-free hemoglobin are known in the art. (U.S. Pat. Nos. 4,584,130, 4,598,064 and 4,600,531). For example, one of these modified hemoglobins, diaspirin crosslinked hemoglobin, is prepared by allowing stroma-free hemoglobin to react with bis(3,5-dibromosalicyl) fumarate in the presence of 2,3-diphosphoglycerate, inositol hexaphosphate or inositol hexasulfate (U.S. Pat. Nos. 4,598,064 and 4,600,531). This treatment modifies stroma-free hemoglobin by covalently linking the lysine-99 residues on the alpha chains of the protein through a fumarate bridge. As a consequence of this intramolecular cross-linking, diaspirin crosslinked hemoglobin has an oxygen affinity equivalent to that of blood. Furthermore, diaspirin crosslinked hemoglobin (molecular weight 64,500) can no longer break down into dimers (molecular weight 32,250). Since the retention time of hemoglobin in the circulatory system increases as the molecular weight of the protein increases, the retention time of diaspirin alpha-alpha crosslinked hemoglobin is four to eight hours, two to four times that of stroma-free hemoglobin. However, this is not a sufficient length of time for utility in the treatment of acute hemorrhage, since an oxygen carrier is needed that can carry oxygen for several days when the patient has lost a considerable amount of blood.

Hemoglobin molecules have also been intermolecularly crosslinked to each other through the use of low-molecular weight crosslinking agents. In particular, K. Bonhard discloses coupling hemoglobin molecules to one another and/or to serum proteins and gelatin derivatives using dialdehydes, optimally followed by the addition of pyridoxal phosphate (U.S. Pat. No. 4,336,248). Bonson et al. disclose crosslinking with a bifunctional or polyfunctional, low-molecular weight crosslinking agent. See U.S. Pat. Nos. 4,001,401, 4,001,200, 4,053,590 and 4,061,736. Typical, known products of intermolecular crosslinking of these types have oxygen-carrying and -delivery properties that are not equivalent to blood ($P_{50}$ of 18–23 for glutaraldehyde-polymerized hemoglobin as compared to $P_{50}$ of 28 for whole blood). Furthermore, known products of intermolecular crosslinking by glutareldehyde are antigenic (D. H. Marks et al., Military Med. Vol. 152, p. 473, 1987).

Similarly, Mock et al. (Fed. Proc. Vol. 34, p. 1458, 1975) and Mazur (U.S. Pat. No. 3,925,344) show the use of low-molecular weight, bifunctional, crosslinking agent for the preparation of intra- and intermolecular crosslinked hemoglobin. The absence of preclinical or clinical reports on the efficacy and safety of this material, which was discovered in 1975, infers that it does not meet the suitability criteria defined above.

Hemoglobin has also been coupled to polymers through the use of low-molecular weight mediators. For example, hemoglobin has been coupled to hydroxyethylstarch (German patent offenlegungsschrift No. 2,616,086); to inulin (K. Ajisaka and Y. Iwashita, "Oxygen carrier for blood substitute", U.S. Pat. No. 4,377,512); and to dextran (J. T. F. Wong, European Patent Application 0,140,640). Similarly, hemoglobin has been coupled to itself and/or to other serum proteins and gelatin derivatives using dialdehyde (3 to 8 carbon atoms) mediators, optionally followed by addition of pyridoxal phosphate (K. Bonhard and U. Boysen, U.S. Pat. No. 4,336,248). Similarly, in U.S. Pat. No. 4,179,337, peptides and polypeptides are coupled to polymers which contain a substantially linear ethereal or carbon-carbon backbone. Polyethylene glycol and polypropylene glycol are preferred. The coupling is accomplished using 10 to 100 molar equivalents of polymer to peptide or more suitably, 15 to 50 molar equivalents of polymer to polypeptide. Coupling must be accomplished with the aid of mediators. In U.S. Pat. No. 4,301,144 (Yuji Iwashita and Katsumi Ajisaka, "Blood Substitute Containing Modified Hemoglobin") hemoglobin is modified by coupling via an amide bond between a mediator-activated, terminal group of a poly(alkylene) glycol and an amino group of hemoglobin. More recent embodiments of this technology (U.S. Pat. Nos. 4,412,989 and 4,670,417) are reported to give monomeric, dimeric and trimeric modified hemoglobins. These embodiments have $P_{50}$ of 21 to 25 and half-times in the circulation of 4 to 8 hours. Furthermore, the materials are so unstable that they must be lyophilized in the presence of stabilizers in order to permit storage. All of these factors indicate that derivatives of this type do not meet the criteria described above.

SUMMARY OF THE INVENTION

Surprisingly, we have found that a mixture of hemoglobin based monomers and oligomers comprising polymerization modified hemoglobin based monomer and oligomers of hemoglobin based monomers, meets the criteria specified above. Namely, the material carries and delivers oxygen to devices, organs and tissues such that normal oxygen tensions are maintained in these environments. The material also has been shown to be non-pyrogenic. The material has been shown to be free of bacterial and/or viral contamination. The material has been shown to be safe and non-toxic. The material is miscible with blood and serum. The material has viscosity, colloid and oncotic properties comparable to blood. Finally, the material has been shown to be retained in the vascular system of mammals for a circulation half-life of at least about thirteen hours and to have a $P_{50}$ at least equivalent to that of hemoglobin in human red cells. It should be noted that the product may also contain a limited amount of high molecular weight polymerized hemoglobin and unmodified hemoglobin monomer.

In particular, the present invention relates to a mixture of hemoglobin based monomers and polymers comprising a polymerization modified based monomer and oligomers of hemoglobin based monomers. In the preferred embodiment a water soluble polyether oxirane is used as the polymerization agent. Additionally, in the preferred embodiment sulfhydryl agents are used to terminate the polymerization and ensure that the mixture is in its most useful oxidation state.

This invention also involves a process to make a mixture of hemoglobin based monomers and oligomers comprising: polymerizing said monomers in the presence of a sufficient amount of a water soluble substance containing three membered rings to make a mixture having a circulation half time of at least thirteen hours and a $P_{50}$ at least equivalent to the $P_{50}$ of hemoglobin in human red cells.

In particular, polyether oxirane is used to complete the polymerization reaction.

It is an object of the invention to provide a mixture having less than about 50% polymerization modified hemoglobin based monomer, less than about 5% high molecular weight polymers of a hemoglobin based composition, and at least about 20% oligomers, but preferably between about 70–80% oligomers of a hemoglobin based composition. The oligomers are comprised of from between 2 to 10 hemoglobin based monomers.

It is a further object of this invention to provide a mixture of hemoglobin based monomers and polymers that have a $P_{50}$ equivalent to or greater than that of hemoglobin in human red cells, that is of a viscosity equal to that of blood, that lacks antigenicity, is not toxic and is sufficiently stable to function as a means for oxygen delivery.

DETAILED DESCRIPTION OF THE INVENTION-BEST MODE

Figure 1:
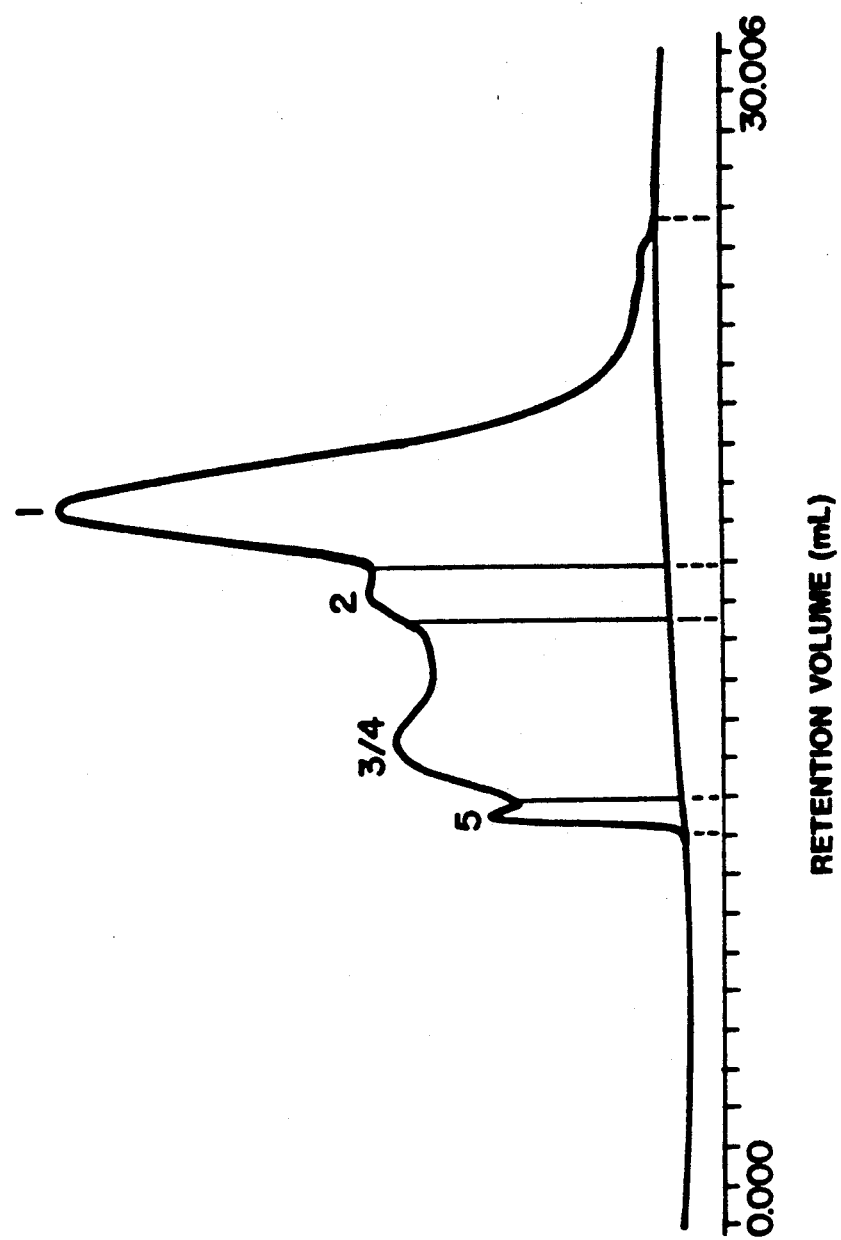
FIG. 1 shows a size exclusion HPLC profile for a hemoglobin mixture prepared according to the presently disclosed process.

The crosslinking may be performed on any one of a number of hemoglobin based compositions, including but not restricted to stroma-free hemoglobin, intramolecularly crosslinked hemoglobin and encapsulated hemoglobin. The preferred embodiment uses a hemoglobin intramolecularly crosslinked with a diaspirin derivative, such as described in U.S. Pat. Nos. 4,598,064 and 4,600,531, both of which are herein incorporated by reference. A brief description of the intramolecular crosslinking with a diaspirin derivative, the preferred embodiment, will suffice here. A description is provided in the above patents. Red blood cells are first washed and lysed to release the hemoglobin. The crude hemolysate is filtered to remove the outer cell membrane or stroma. The hemoglobin is then washed and concentrated, and placed in a reactor with sodium tripolyphosphate and bis(3,5-dibromosalicyl) fumarate. The resulting diaspirin crosslinked hemoglobin has a weight of 64,500 Daltons.

The polymerization agents used in this invention are water soluble three member heterocyclic ring compounds including oxiranes, aziranes, and thiiranes. The polymerization agent of choice is any one of the water soluble polyether oxirane compounds, preferably long chain polyether oxiranes having between 15 and 75 atoms in the chain. One polyether oxirane is Denacol TM (Nagase Chemical Co.). Denacol is the tradename for several types of oxirane compounds which are mixtures of mono-, di-, triglycidyl ethers, esters and N-glycidyl compounds. Denacol TM EX-810, EX-313, EX-830, EX-841 and EX-861 have been evaluated.

A number of process variables influence the characteristics of the final product. These parameters include: the buffer, ratio of polymerization agent to hemoglobin based composition, and polymerization temperature.

The polymerization of the hemoglobin based solution occurs in the presence of a buffer, including TRIS, HEPES and phosphate buffer. The preferred buffer is sodium carbonate.

The temperature at which the polymerization is carried out can be controlled to determine certain product characteristics. Thus, if the polymerization is conducted at temperatures of about 0° to 10° C., the polymerized product has a $P_{50}$ less than blood, i.e., less than 28 mm Hg. Furthermore, if the polymerization is conducted at temperatures greater than 10° C., the polymerized product has $P_{50}$ more similar to that of blood. Alternatively, if the polymerization is completed at higher temperatures, the polymerized product has a $P_{50}$ greater than or equal to that of blood.

Molar ratios of polymerization agent to hemoglobin based composition of 10 to 15 are preferred but the ratio can range from 1:1 to 100:1. If the molar ratio of polymerization agent to hemoglobin based composition is greater than 15, the $P_{50}$ of the polymerization product is substantially right-shifted from that of hemoglobin in the red cell.

A mixture of hemoglobin based monomers and polymers is formed by this process. The mixture obtained by the above discussed polymerization method has less than about 50% polymerization modified hemoglobin based monomers, but preferably less than about 10% polymerization modified hemoglobin based monomers. (A "monomer" is a hemoglobin unit in the tetrameric form.) Additionally, it has less than about 5% high molecular weight polymers of a hemoglobin based composition. And, finally it has at least about 20% oligomers of a hemoglobin based composition, but preferably between about 70-80% oligomers of a hemoglobin based composition. The oligomers are comprised of from between 2 to 10 hemoglobin based monomers. It should be noted that the mixture may contain only oligomers and does not necessarily include polymerization modified hemoglobin based monomers or high molecular weight polymers, or unmodified hemoglobin monomers.

The distribution of monomers and polymers in the mixture can be ascertained by size exclusion chromatography (SEC). Size exclusion chromatography has its basis in the observation that, within certain limits which are determined by the pore size of the chromatographic stationary phase, proteins are separated on the basis of their molecular weights. The order of elution from the column is highest to lowest molecular weight; proteins having molecular weights exceeding the upper limit of retention on the stationary phase are eluted earliest and are detected as a sharp band coincident with the void volume of the chromatographic column, whereas those having lower molecular weights are eluted later, as somewhat broader peaks, in order of decreasing molecular weight. The composition of a mixture of proteins is determined by the ratio of the area of the peak response for each protein component to the sum of the areas of all protein components in the mixture. Thus, as FIG. 1 shows, a size exclusion chromatographic profile of a hemoglobin based mixture formed by the presently disclosed process shows less than 1% high molecular weight polymer as Band 5; between about 70-80% oligomers as Bands 2, 3 and 4; and between about 20-30% polymerization agent modified monomer as Band 1.

Figure 2:
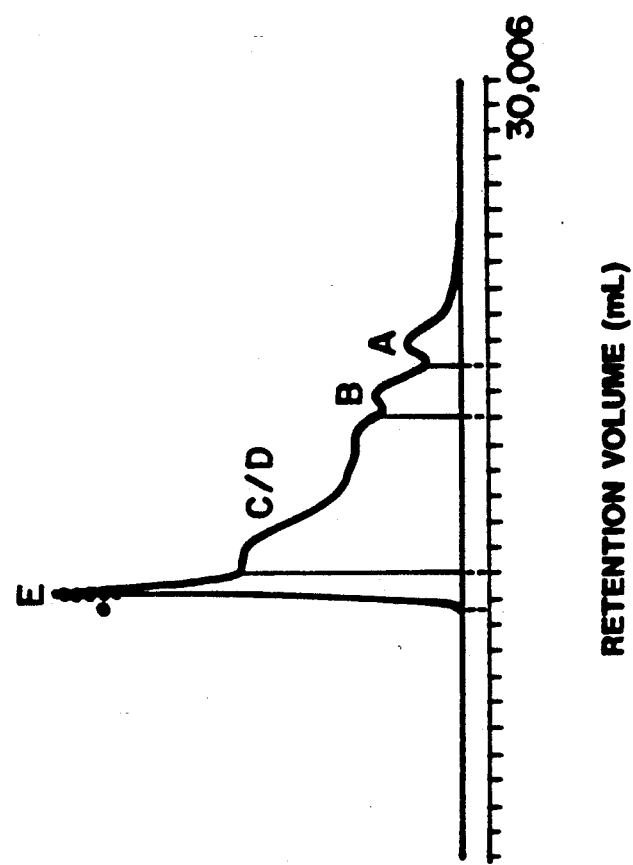
FIG. 2 shows a size exclusion HPLC profile for a glutaraldehyde polymerized hemoglobin.

This profile is to be contrasted with that of a glutaraldehyde polymerized hemoglobin. See FIG. 2. The size exclusion chromatogram of glutaraldehyde-polymerized hemoglobin shows about 10% high molecular weight polymer as Band E; between about 60–70% oligomers as Bands C and D; about 10% dimers as Band B; and about 10% monomer as Band A.

Furthermore, we have identified reagents that concomitantly quench the polymerization and ensure that the product is in its most useful oxidation state. Namely, we have found that the quenching agents, L-cysteine, N-acetyl-L-cysteine or the combinations of these amino acids with ethanolamine, convert any methemoglobin (iron in its +3 oxidation state) that may be present in the final product mixture to modified hemoglobin (iron in its +2 oxidation state). This conversion is key, because methemoglobin does not carry or deliver oxygen. Although any combination of the named reagents may be used, the absence of undesirable side reactions when N-acetyl-L-cysteine was used as the quenching agent, renders this amino acid the most suitable for use.

The mixture of hemoglobin based monomers and polymers comprised of polymerization modified hemoglobin based monomer and oligomers of hemoglobin based monomers carries and delivers oxygen to devices, organs and tissues so that normal oxygen tensions are maintained in these environments, i.e., a $P_{50}$ of at least 28 mm of Hg at 37° C. The mixture is nonpyrogenic and free of bacterial and/or viral contamination. The mixture is safe and nontoxic. It is also miscible with blood and serum. The mixture has viscosity, colloid and oncotic properties comparable to those of blood. The mixture is retained in the vascular system of a mammal for a circulation half-life of at least thirteen hours and is known to have a $P_{50}$ at least equivalent to that of hemoglobin in a red cell. Furthermore, the mixture was found not to hinder erythropoeisis.

EXAMPLE 1. POLYMERIZATION OF DIASPIRIN CROSSLINKED HEMOGLOBIN WITH DENACOL TM (EX-861) AT 25° C.

The pH of 10 mL of diaspirin crosslinked hemoglobin (24.3 g/dL in Ringer's lactate solution) was adjusted to 9.0 (5° C.) by the addition of 0.3 mL of 1M sodium carbonate. The solution was deoxygenated by successive vacuum/nitrogen cycles for one hour at 25° C. An aqueous solution of Denacol TM EX-861 was added, and the reaction mixture was stirred under nitrogen at 25° C. The reactions were monitored by size exclusion chromatography (SEC), using TSKGel TM G4000SW and TSKGel TM G3000SW columns connected in series and a mobile phase consisting of a 9:1 (V/V) ratio of 50 mM phosphate, pH 6.5/isopropanol delivered at 1 mL/min. Experimental data are summarized in the following Table 1.

TABLE 1

POLYMERIZATION OF DIASPIRIN CROSSLINKED HEMOGLOBIN WITH A POLYMERIZATION AGENT

| Reaction | Molar Ratio Polymerization Agent: Hemoglobin | Time (Hr.) | SEC Profile*, % | | | |
|---|---|---|---|---|---|---|
| | | | 1 | 2 | 3/4 | 5 |
| 550 | 15/1 | 24 | 51 | 17 | 32 | 0 |
| 551 | 25/1 | 23.5 | 46 | 17 | 37 | 0 |
| 557 | 10/1 | 19 | 46 | 18 | 35 | 1 |

*The SEC retention volumes were Band 1, 17–18 mL; Band 2, 15–16 mL; Band 3/4, 12–14 mL; and Band 5, 10 mL. Under the HPLC conditions the retention volume of diaspirin crosslinked hemoglobin is about 21 mL. The decreased retention volume of Band 1 indicates that diaspirin crosslinked hemoglobin has been extensively modified by the polymerization agent.

EXAMPLE 2 POLYMERIZATION OF DIASPIRIN CROSSLINKED HEMOGLOBIN WITH LONG-CHAIN POLYMERIZATION AGENT AT 5° C.-25° C.

Polymerizations of diaspirin crosslinked hemoglobin with Denacol TM EX-830, EX-841 and EX-861 have been completed under the following conditions. The pH of 10 mL of diaspirin crosslinked hemoglobin (24.3 g/dL in Ringer's lactate solution) was adjusted to 9.0 (5° C.) by the addition of 0.3 mL of 1M sodium carbonate. The solution was deoxygenated by successive vacuum/nitrogen cycles for 1 hour at 25° C. An aqueous solution of Denacol TM was added, and the reaction mixture was stirred under nitrogen at 25° C. or 5° C. The reactions were monitored by size exclusion chromatography, using TSKGel TM G4000SW and TSKGel TM G3000SW columns connected in series and a mobile phase consisting of a 9:1 (V/V) ratio of 50 mM phosphate, pH 6.5/isopropanol delivered at 1 mL/min. At 5° C. the molar ratio of polymerization agent/hemoglobin ranged from 40:1 to 60:1 and the reaction was quenched after 4 or 5 days; whereas at 25° C. the corresponding molar ratio ranged from 15:1 to 25:1 and the reaction time was a day or less. Experimental data are summarized in Table 2. The viscosities of ca. 10 g/dL solutions of these derivatives ranged from 1.9–2.5 centistokes, and the oxygen-binding curves were all right-shifted compared to that of native hemoglobin.

TABLE 2

POLYMERIZATION OF DIASPIRIN CROSSLINKED HEMOGLOBIN WITH LONG-CHAIN POLYMERIZATION AGENT AT 25° C.

| Reaction | Denacol TM | Molar Ratio Polymerization Agent: Hemoglobin | Time (Hr) | SEC Profile, % Band | | | |
|---|---|---|---|---|---|---|---|
| | | | | 1 | 2 | 3/4 | 5 |
| 538 | EX-830 | 15/1 | 22 | 35 | 17 | 45 | 2 |
| 539 | EX-830 | 25/1 | 19 | 33 | 16 | 46 | 4 |
| 542 | EX-841 | 15/1 | 21 | 41 | 18 | 40 | 0 |
| 543 | EX-841 | 25/1 | 19 | 41 | 18 | 40 | 0 |
| 550 | EX-861 | 15/1 | 24 | 51 | 17 | 32 | 0 |
| 551 | EX-861 | 25/1 | 23.5 | 46 | 17 | 37 | 0 |

The SEC retention volumes were Band 1, 17–18 mL; Band 2, 15–16 mL; Band ¾, 12–14 mL; and Band 5, 10 mL. Under the HPLC conditions the retention volume of diaspirin crosslinked hemoglobin is about 21 mL. The decreased retention volume of Band 1 indicates that diaspirin crosslinked hemoglobin has been extensively modified by the Denacol TM.

EXAMPLE 3 DIASPIRIN CROSSLINKED HEMOGLOBIN POLYMERIZATION WITH LONG-CHAIN POLYMERIZATION AGENT AT 5° C.

Polymerization of diaspirin crosslinked hemoglobin by Denacol TM (long chain) has also been studied at 5° C. As expected, polymerization proceeded more slowly and gave chromatographic profiles somewhat different from those obtained in reaction at 25° C. The experimental data (Table 3) indicate that reaction at 5° C. minimizes the percentage of high molecular weight polymers in the product mixtures. After 4–5 days the retention volumes of Band 1 were shifted from the usual 20 mL characteristic of diaspirin crosslinked hemoglobin to volumes of 16.5–17.2 mL, volumes that usually correspond to dimers (Band 2), while the retention volumes of Band 2 shifted from the 17.5 mL usually seen for dimers to the 15.4–16.0 mL range characteristic of trimers.

At 5° C. less oxidation to methemoglobin was seen. Like the products from polymerization at 25° C., ca. 10 g/dL solutions of these materials had viscosities that ranged from 1.5–2.2 centistokes. In contrast to the product mixtures from reactions at 25° C., the oxygen-binding curves of these materials were left-shifted and less cooperative than that of native hemoglobin.

TABLE 3

DIASPIRIN CROSSLINKED HEMOGLOBIN POLYMERIZATION WITH LONG-CHAIN POLYMERIZATION AGENT AT 5° C.

| Reaction | Molar Ratio Polymerization Agent/ | Time | SEC Profile, % | | | |
|---|---|---|---|---|---|---|
| Decanol TM | Hemoglobin | (Days) | 1 | 2 | 3/4 | 5 |
| 536 | EX-830 | 40/1 | 4 | 40 | 19 | 41 | 0 |
| 537 |  | 60/1 | 4 | 36 | 16 | 43 | 0 |
| 540 | EX-841 | 40/1 | 4 | 47 | 23 | 30 | 0 |
| 541 |  | 60/1 | 4 | 44 | 22 | 34 | 0 |
| 552 | EX-861 | 40/1 | 5 | 45 | 19 | 36 | 0 |
| 553 |  | 60/1 | 5 | 41 | 18 | 39 | 1 |

EXAMPLE 4 EFFECTS OF QUENCHING AGENTS

One serious problem associated with the synthesis of polymerized hemoglobin is the oxidation of hemoglobin to methemoglobin (which does not carry or deliver oxygen). For example, the percent methemoglobin increased from 3.3% to as much as 17% during polymerization at 25° C. To counter this, we evaluated ethanolamine and/or N-acetyl-L-cysteine as reagents to concomitantly quench the polymerization and reduce the methemoglobin to hemoglobin. The experiments were performed as follows. Diaspirin crosslinked hemoglobin (19 g/dL) was deoxygenated and polymerized with Denacol TM EX-861 at 25° C. in sodium carbonate buffer, pH 9.0, employing a Denacol TM diaspirin crosslinked hemoglobin molar ratio of 20:1. After 24 hours, a deoxygenated solution of 2M ethanolamine hydrochloride, pH 9.0, or 2M N-acetyl-L-cysteine, pH 9.0, was added. The reaction mixture was stirred overnight (15 hours) at 5° C. under either aerobic or anaerobic conditions. The next day the size exclusion chromatography profiles and percent methemoglobin in the product mixtures were determined.

We found that under aerobic conditions the addition of ethanolamine in amine to polymerization agent molar ratios ranging from 3:1 to 6:1 largely quenches polymerization; however, no methemoglobin reduction occurs. In contrast, under aerobic conditions the addition of N-acetyl-L-cysteine in this same range of molar ratios both quenches the polymerization and reduces the percent methemoglobin in the product. The effect of addition of N-acetyl-L-cysteine (NAC) under anaerobic conditions is even more striking, as shown in Table 4. Molar ratios of quenching agent to polymerization agent of 3:1 or 4:1 are sufficient to quench the reaction and reduce the percent methemoglobin from more than 24% to less than 10%.

TABLE 4

EFFECTS OF QUENCHING AGENTS[a]

| Molar Ratio | Time | MetHb | SEC Profile, % | | | |
|---|---|---|---|---|---|---|
| NAC/Denacol TM | (Hr) | (%) | 1 | 2 | 3/4 | 5 |
| 0/1 | 0 | 25.1 | 47 | 14 | 34 | 5 |
| 0/1 | 15 | 23.6 | 29 | 11 | 29 | 31 |
| 3/1 | 15 | 7.5 | 36 | 14 | 42 | 6 |
| 4/1 | 15 | 7.7 | 34 | 16 | 43 | 6 |
| 5/1 | 15 | 12.5 | 35 | 15 | 43 | 6 |
| 6/1 | 15 | 8.8 | 34 | 15 | 44 | 6 |

[a]Anaerobic conditions.
[b]The SEC retention volumes were: diaspirin crosslinked hemoglobin (20–21 mL; absent from all product mixtures); Band 1 (substituted diaspirin crosslinked hemoglobin monomers), ca. 18 mL; Band 2 (substituted diaspirin crosslinked hemoglobin dimers), ca. 16 mL; Bands 3/4 (substituted diaspirin crosslinked hemoglobin oligomers), ca. 12–16 mL; and Band 5, high molecular-weight polymers of substituted diaspirin crosslinked hemoglobin, 10 mL.

EXAMPLE 5 POLYMERIZATION OF HEMOGLOBIN BASED SOLUTION

To permit biological screening of polymerized diaspirin crosslinked hemoglobin, the polymerized hemoglobin has been produced both at the small- and the large-laboratory scale. The process was completed at the small scale to verify the suitability of process parameters prior to the larger scale reaction. At the former scale, 10 mL of deoxydiaspirin crosslinked hemoglobin (20.1 g/dL concentration containing 6.4% of methemoglobin) in 0.036M sodium carbonate buffer, pH 9.0, was treated with an aqueous solution of Denacol TM EX-861 (15:1 molar ratio of polymerization agent to hemoglobin). The reaction mixture was stirred at 25° C. under nitrogen for 24 hours. During this time the percent methemoglobin increased to 17.4%. The reaction mixture was cooled to 5° C. and a solution of 2M NAC, pH 8.95, was added (quenching agent to polymerization agent ratio, 4:1). The resulting solution was stirred under nitrogen overnight at 5° C. The percent methemoglobin was reduced to 9.7%. The reaction mixture was diluted to a volume of 150 mL with Ringer's lactate solution and diafiltered through a 10,000 Dalton MWCO hollow fiber cartridge to reduce the volume to 100 mL. The dilution/concentration process was repeated until 3 L of filtrate was collected. The solution was concentrated to a volume of 45 mL. The resulting product was characterized analytically, as shown in Table 5.

TABLE 5

ANALYTICAL PROFILE OF POLYMERIZATION PRODUCT

| | |
|---|---|
| [Hb], g/dL[a] | 10.6 |
| % Methemoglobin[a] | 10.0 |
| SEC Profile[b] | Band 1   50% |
| | Band 2   16% |
| | Band 3/4   34% |
| | Band 5   0% |
| Viscosity at 37° C. | 2.1 centistokes |
| $P_{50}$ | 77 mm Hg |
| Hill Constant | 1.3 |

[a]By spectrophotometry.
[b]See Table 4 for explanation of SEC bands.
[c]The oxygen affinity was determined by Hemox analyzer in Hemox buffer at 37° C. using oxygen.

EXAMPLE 6 POLYMERIZATION OF HEMOGLOBIN BASED SOLUTION

The reaction was repeated under aseptic conditions at the large laboratory scale. The processing system incorporated an Applikon, 3-L, jacketed fermentor that was equipped with precalibrated sensors for oxygen (an Ingold polarographic oxygen electrode), pH, and temperature. Nine, 1-L units of diaspirin crosslinked hemoglobin were thawed, pooled and concentrated to a volume of approximately 3 L. The resulting diaspirin crosslinked hemoglobin solution had a concentration of 30.1 g/dL. A 1.1 L portion of this solution was transferred to the fermenter and the pH of the solution was adjusted to 9.0 (5° C.) by the addition of 0.05M sodium carbonate. Water was added to attain a volume of 1.4 L. The resulting solution was deoxygenated at 25° C.

The extent of deoxygenation was monitored by Co-oximeter analysis of samples that were withdrawn anaerobically during the deoxygenation. A value of 4.8% oxydiaspirin crosslinked hemoglobin was reached, corresponding to a $P_{O2}$ probe reading of 0.103 ppm oxygen. Then a solution of Denacol TM EX-861 (polymerization agent to hemoglobin molar ratio 15:1) in water was added, and the reaction was stirred overnight. When size exclusion chromatographic monitoring indicated an appropriate degree of polymerization had been achieved, the reaction mixture was cooled to 13° C. and a solution of 2M N-acetyl-L-cysteine pH 9.0 (quenching agent to polymerization agent molar ratio 4:1) was added. The reaction was stirred overnight at 5° C. After filtration and diafiltration against Ringer's lactate solution, the product was obtained. The analytical profile of the product is shown in Table 6.

TABLE 6

ANALYTICAL PROFILE OF POLYMERIZATION PRODUCT

| | | |
|---|---|---|
| [Hb], g/dL[a] | 0.4 | |
| % Methemoglobin[a] | 4.0 | |
| GPC Profile[b] | Band 1 | 52% |
| | Band 2 | 11% |
| | Band 3/4 | 33% |
| | Band 5 | 3% |
| pH at 37° C. | 7.23 | |
| $P_{50}$[c] | 68.5 mm Hg | |
| Oncotic Pressure | 46.2 mm Hg | |
| Sterility | Sterile | |
| Pyrogenicity | <0.125 EU/mL | |
| Filterability (per 5 min.) | 16 mL | |

[a] by spectrophotometry.
[b] See Table 4 for an explanation of the SEC bands.
[c] The oxygen affinity was determined by Hemox analyzer in Hemox buffer at 37° C. using oxygen.

It was determined that the polyether oxirane polymerization product did not cause complement activation or leukocyte aggregation. In particular, no increase in complement activation was observed upon administration of this polymerization product to mice. Similarly, the leukocyte count did not substantially change upon administration of this polymerization product. The absence of microorganisms was determined through aerobic and anaerobic culturing. Similarly, the polyether oxirane polymerization product behaved similarly to blood. Colloid and oncotic properties were established since test subjects did not lose blood pressure upon administration of this polymerization product. See Example 8. The polymerization product was also observed to be miscible with blood in that if blood samples were drawn, two different layers were not observed. Also, it should be noted that this polymerization product was not observed to hinder erythropoeisis.

EXAMPLE 7 EVALUATION OF CIRCULATION HALF-LIFE

Polyether oxirane polymerized hemoglobin was evaluated in male Sprague-Dawley rats. A bolus injection of the mixture equivalent to 20% of the animals' blood volume was given through a QuickCath TM in the tail vein. Blood was withdrawn through an indwelling carotid catheter or tail vein at sampling times ranging from 0.25 to 92 hours. Half lives were determined from the total absorbance of the plasma samples at 414 nm. The average half-life was 13.2 hours.

The monomeric, dimeric, and polymerized forms of the mixture in the plasma samples were separated by size exclusion chromatography. The contribution of each species to the total plasma absorbance at 414 nm was calculated from the area % of the peaks in the chromatograms and half-life of the dimeric and larger species was 15 hours; the monomer had a significantly shorter half-life (8 hours).

EXAMPLE 8 EXAMINATION OF RENAL FUNCTION

The effects of a topload infusion of polyether oxirane polymerized diaspirin crosslinked hemoglobin solution on renal function were compared to those of a control solution of albumin in lactated Ringer's solution with oncotic pressure adjusted to be similar to that of polyether oxirane polymerized diaspirin crosslinked hemoglobin solution. Renal function was evaluated in male, Sprague Dawley rats by determining renal blood flow, glomerular filtration rate and excretion rates of the major solutes. The test article was a solution containing approximately 10 g/dL of hemoglobin polymerized according to Example 6 and was diluted in Lactated Ringer's solution. The control article was Lactated Ringer's solution containing human serum albumin at a concentration which resulted in a similar colloid osmotic pressure to that of the 10 g/dL polymerized hemoglobin solution. In summary, the experimental data show that renal function is maintained following infusion of polymerized hemoglobin-based solution.

In these experiments each rat was anesthetized with an intraperitoneal injection and catheters were implanted in both jugular veins for infusions, carotid artery for obtaining blood samples and monitoring mean arterial pressure (MAP), and urinary bladder for collecting urine samples. A tracheostomy was performed to facilitate respiration. Body temperatures were monitored throughout the study and maintained at approximately 37°–38° C. Following placement of the catheters, each animal received an infusion of saline over the first hour to stabilize renal function and replace surgical losses of fluid. A bolus of saline containing 0.5 μCi each of $^{125}$I-iothalamate and $^{131}$I-hippuran, was infused first, followed by the slow infusion of normal saline solution containing approximately 0.5 μCi/mL of $^{125}$I-iothalamate and $^{131}$I-hippuran. At thirty minute intervals, six sequential urine samples were collected. Blood samples were obtained at the midpoint of urine samples #1, 3 and 5, and at the end of the study (Table 7). The rats were infused with 30 mL/kg polymerized hemoglobin solution or albumin solution during the initial part of urine collection #2. See Table 7.

TABLE 7

| | Time Line of Sample Collection Periods | | | | | | | | | | | | | |
|---|---|---|---|---|---|---|---|---|---|---|---|---|---|---|
| Time (min) | 0 | 15 | 30 | 45 | 60 | 75 | 90 | 105 | 120 | 135 | 150 | 165 | 180 | 195 |
| Urine Sample Collection | | 1 | | 2 | | 3 | | 4 | | 5 | | 6 | | |
| Blood Sample Collection | | 1 | | | | 2 | | | 3 | | 3 | | | 4 |
| Test Article Infusion | | 1 | | | | | | | | | | | | |

Urine flow rates were determined by measuring the volume of urine excreted during each time period and dividing by the duration of the collection in minutes. Arterial blood samples were collected anaerobically and analyzed for $pO_2$, $PCO_2$, pH, $HCO_3-$, and hematocrit. Urine and plasma samples were also analyzed for radioisotope counts ($^{125}I$-iothalamate and $^{131}I$-hippuran). $^{125}I$-iothalamate counts were corrected for $^{131}I$-hippuran counts.

Glomerular filtration rate was measured by determining the clearance of $^{125}I$-iothalamate, a solute which is filtered, but is not reabsorbed, secreted, or metabolized by the kidney. Effective renal plasma flow, that portion of total renal plasma flow that has direct contact with the renal tubules, was measured by determining the clearance of $^{131}I$-hippuran, a solute which is filtered and secreted, but not reabsorbed or metabolized by the kidney.

Upon completion of the clearance experiments, with the animals remaining anesthetized, they were exsanguinated and complete necropsies were performed. Samples of heart, lungs, liver, and both kidneys were collected for histopathological evaluation.

Figure 3:
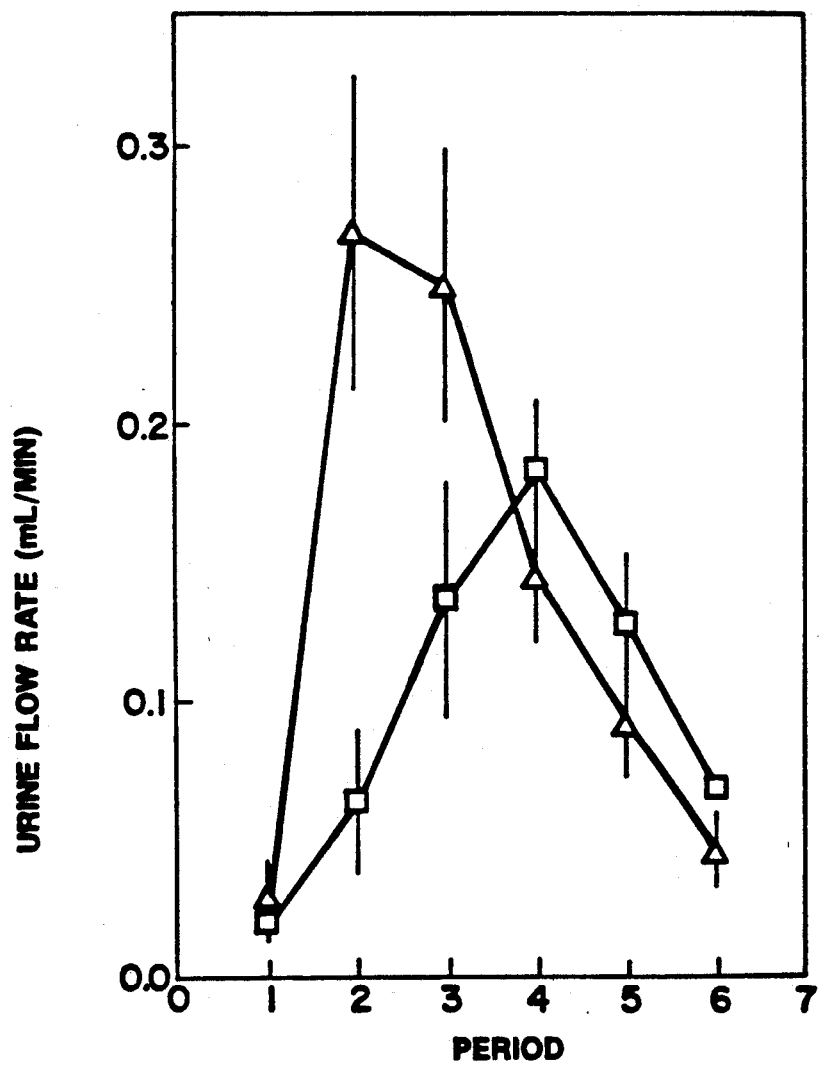
FIG. 3 shows the effect of infusion of polyether oxirane polymerized hemoglobin on urine flow rate as compared to infused control solutions of albumin.
Figure 4:
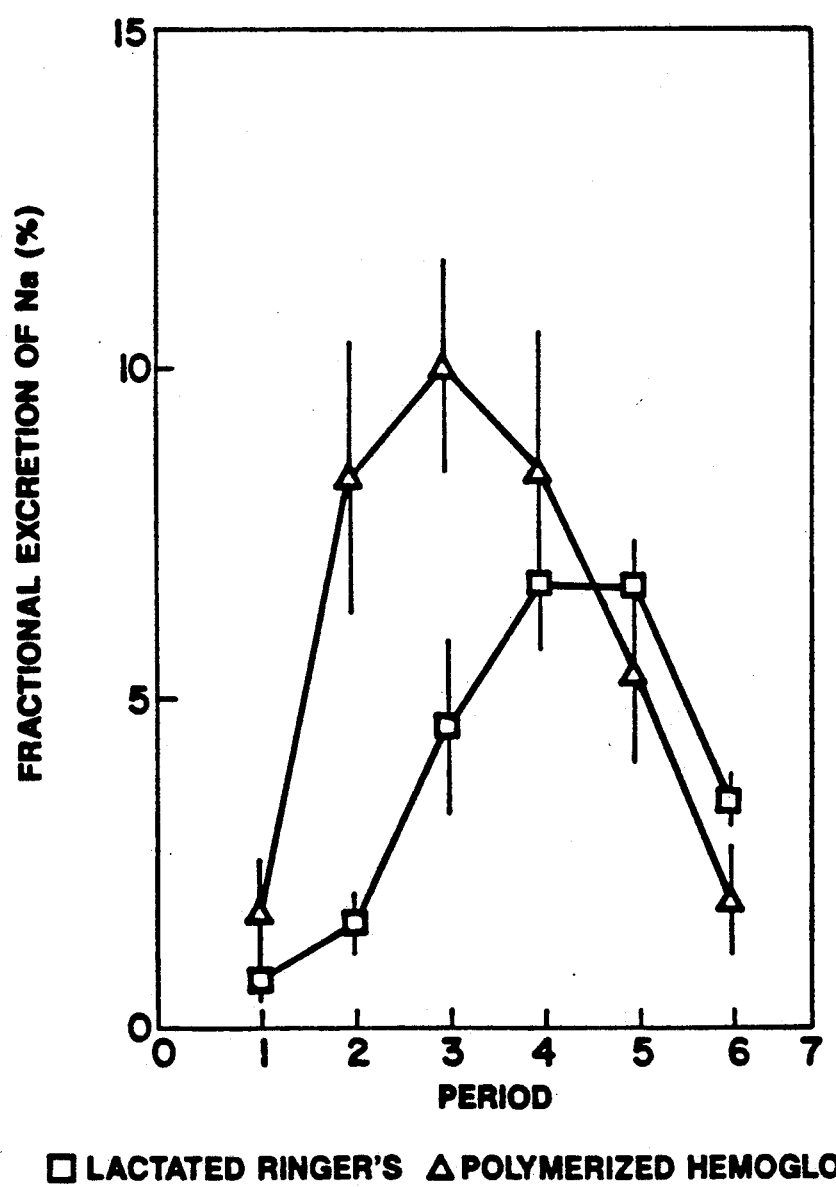
FIG. 4 shows the effect of infusion of polyether oxirane polymerized hemoglobin on fractional excretion rates of sodium as compared to infused control solutions of albumin.

Table 8 compares the effects of polymerized hemoglobin solution and albumin solution on renal function. All results shown in the tables are reported as means±SEM of 5 or 6 rats. Polymerized hemoglobin solution induced moderate diuresis, i.e. an increase in urine flow rate. (FIG. 3 and Table 8) and a small increase in the fractional excretion rates of sodium (FIG. 4 and Table 8) and phosphorus (Table 8) as compared to albumin solution controls. This diuretic effect is probably related to the volume of the infusion solution.

TABLE 8

| Effects of Polymerized Hemoglobin Solution and Lactated Ringer's Solution on Renal Function | | | | | | |
|---|---|---|---|---|---|---|
| Period | 1 | 2 | 3 | 4 | 5 | 6 |
| URINE FLOW RATE (uL/min) | | | | | | |
| LR | 19 ± 6 | 63 ± 26 | 137 ± 43 | 183 ± 26 | 128 ± 25 | 69 ± 3 |
| DPDCLHb | 28 ± 12 | 269 ± 56 | 251 ± 48 | 145 ± 23 | 92 ± 19 | 46 ± 13 |
| GLOMERULER FILTRATION RATE (mL/MIN) | | | | | | |
| LR | 2.18 ± .22 | 2.17 ± 0.38 | 2.31 ± 0.17 | 2.25 ± 0.09 | 1.66 ± 0.23 | 2.47 ± 0.10 |
| DPDCLHb | 1.7 ± 0.16 | 2.54 ± 0.24 | 2.15 ± 0.47 | 1.87 ± 0.34 | 1.64 ± 0.32 | 2.01 ± 0.83 |
| EFFECTIVE RENAL PLASMA FLOW (mL/MIN) | | | | | | |
| LR | 6.22 ± 0.53 | 5.63 ± 0.60 | 5.31 ± 0.70 | 5.04 ± 0.16 | 3.50 ± 0.48 | 5.52 ± 0.46 |
| DPDCLHb | 4.29 ± 0.65 | 6.17 ± 0.70 | 5.22 ± 1.31 | 4.66 ± 0.83 | 4.05 ± 0.76 | 5.51 ± 1.12 |

Results shown in the Tables are reported as means ± SEM of 6 rats, except for period #6 of the polyether oxirane polymerized hemoglobin group in which n = 5.

Figure 5:
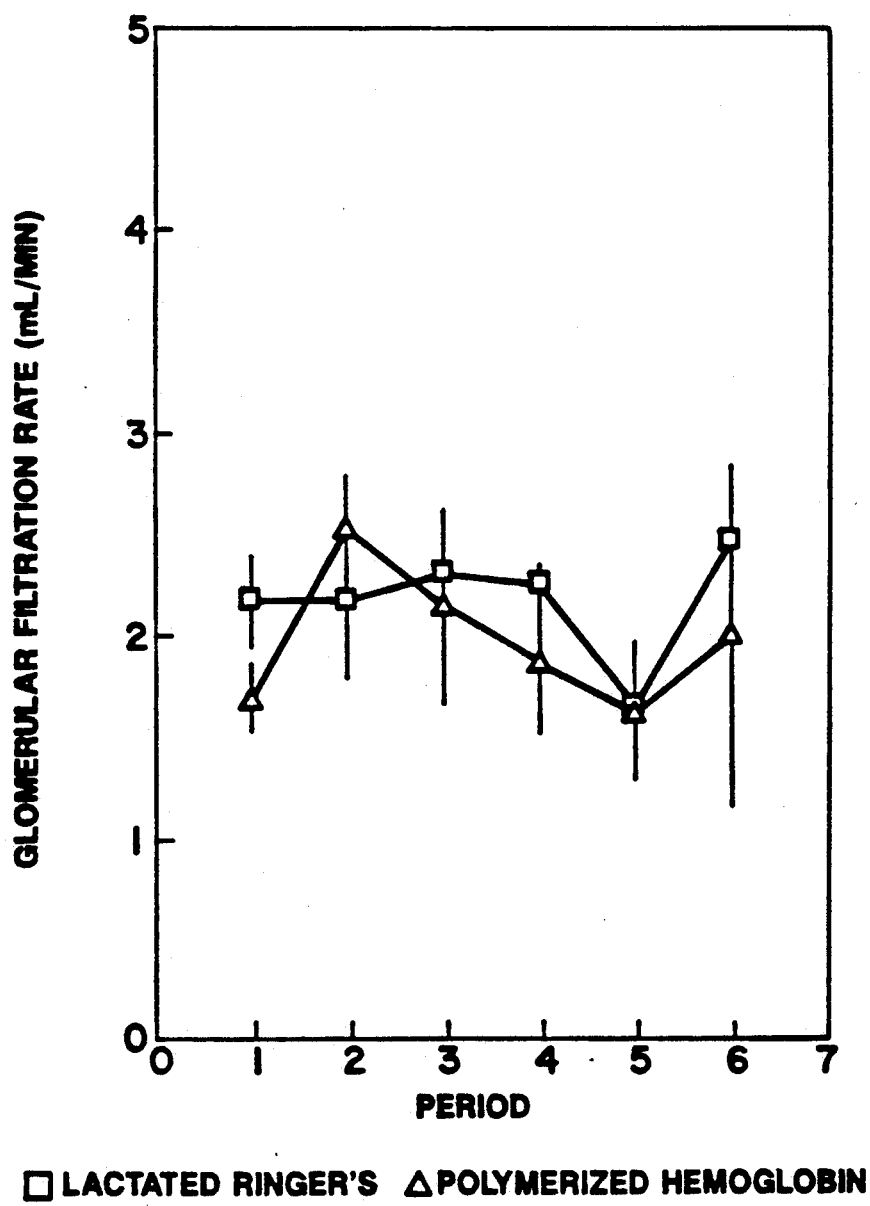
FIG. 5 shows the effect of infusion of polyether oxirane polymerized hemoglobin on glomerular filtration rate as compared to infused control solutions of albumin.

Glomerular filtration rate (FIG. 5 and Table 8) and effective renal plasma flow (Table 8) of the polymerized hemoglobin solution group were increased relative to those of the albumin group, but the change was a functional one that did not impair renal activity. Creatinine clearance was variable in both groups.

Figure 6:
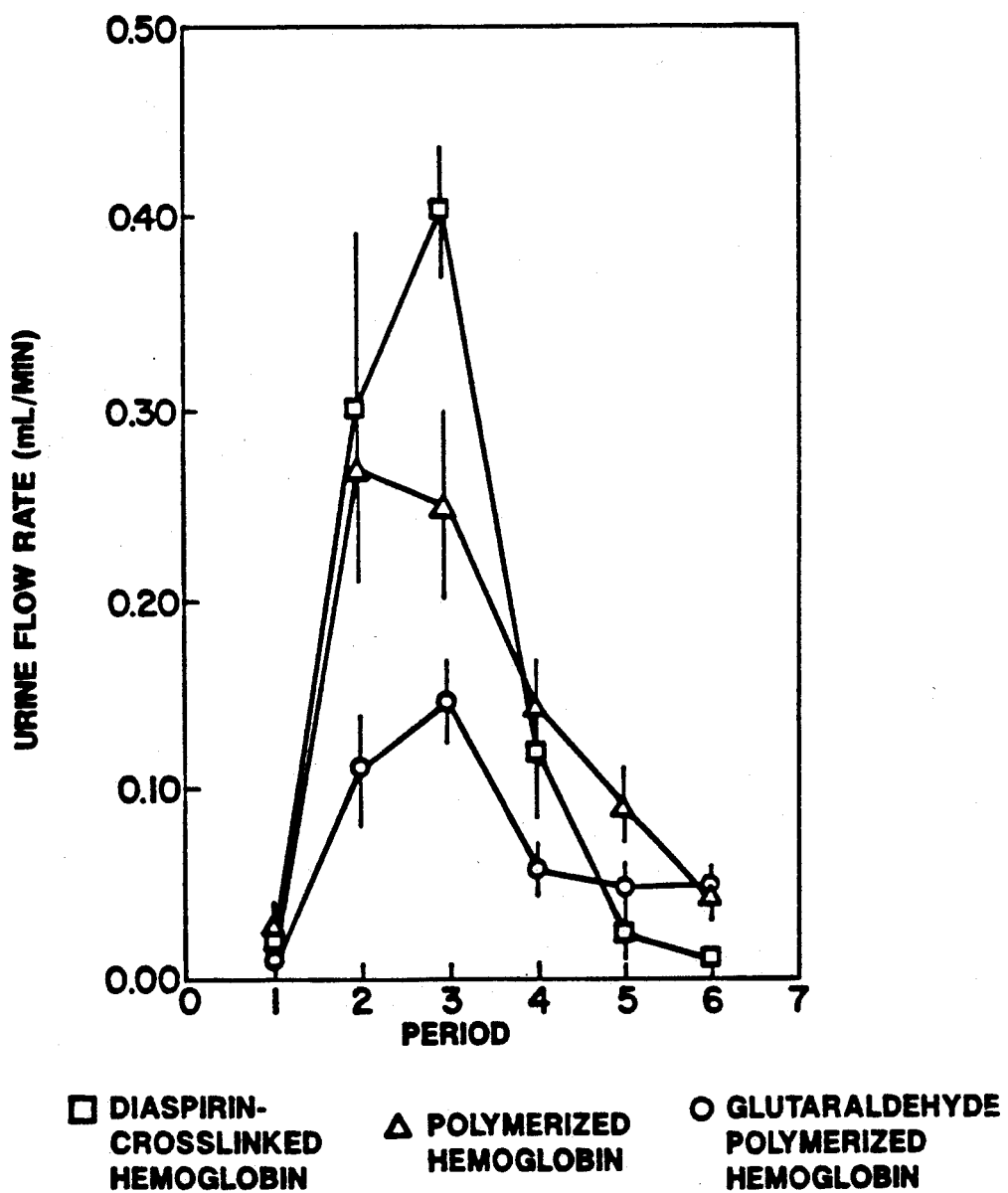
FIG. 6 shows the effect of infusion of polyether oxirane polymerized hemoglobin on urine flow rate as compared to infusions of diaspirin crosslinked hemoglobin and glutaraldehyde polymerized hemoglobin.
Figure 7:
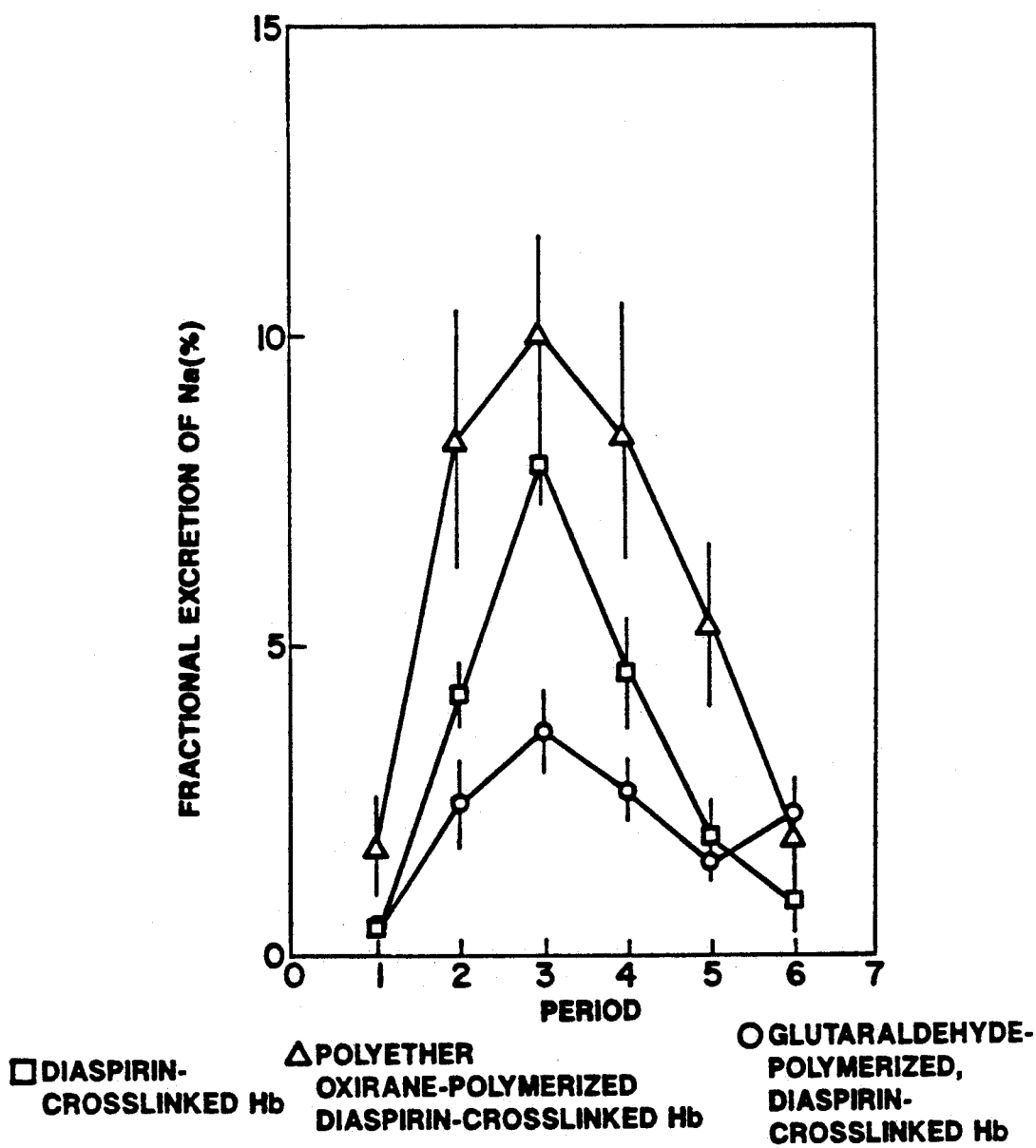
FIG. 7 shows the effect of infusion of polyether oxirane polymerized hemoglobin on fractional excretion rate of sodium as compared to infusions of diaspirin crosslinked hemoglobin and glutaraldehyde polymerized hemoglobin.

FIGS. 6 and 7 compare the effects of topload infusion of polyether oxirane polymerized hemoglobin solution to diaspirin crosslinked hemoglobin and gluteraldehyde polymerized diaspirin crosslinked hemoglobin. The effect of polyether oxirane polymerized hemoglobin solution on urine flow rate is intermediate between the large degree of diuresis induced by diaspirin crosslinked hemoglobin, and the minimal diuresis induced by gluteraldehyde polymerized diaspirin crosslinked hemoglobin (FIG. 6), while the natriuresis induced by polymerized hemoglobin solution is slightly increased as compared to the other two groups.

Table 9 depicts the effects of polymerized hemoglobin solution on solutes. An increase in plasma creatinine was similarly observed following infusion of gluteraldehyde polymerized diaspirin crosslinked hemoglobin. Sodium, potassium, and phosphorus levels were increased during the basal period in the polymerized hemoglobin solution group, but decreased to normal levels as observed in the albumin solution control group.

TABLE 9

| Effects of Polyether Oxirane Polymerized Hemoglobin Solution on Plasma Concentrations of Solids | | | | |
|---|---|---|---|---|
| Period | 1 | 2 | 3 | 4 |
| PLASMA UREA NITROGEN (mg/dL) | | | | |
| LR | 14 ± 1 | 13 ± 1 | 11 ± 1 | 11 ± 1 |
| DPDCLHb | 16 ± 1 | 13 ± 1 | 13 ± 1 | 13 ± 1 |
| PLASMA CREATININE (mg/dL) | | | | |
| LR | 0.4 ± 0.0 | 0.5 ± 0.0 | 0.5 ± 0.0 | 0.5 ± 0.0 |
| DPDCLHb | 0.5 ± 0.0 | 0.7 ± 0.0 | 0.7 ± 0.0 | 0.6 ± 0.1 |
| PLASMA PHOSPHORUS (mg/dL) | | | | |
| LR | 7.9 ± 0.6 | 7.7 ± 0.4 | 7.7 ± 0.2 | 8.1 ± 0.2 |
| DPDCLHb | 8.2 ± 0.2 | 7.3 ± 0.2 | 8.6 ± 1.3 | 7.3 ± 0.2 |
| PLASMA TOTAL PROTEIN (mg/dL) | | | | |
| LR | 4.7 ± 0.2 | 5.5 ± 0.3 | 5.9 ± 0.3 | 5.6 ± 0.3 |
| DPDCLHb | 4.8 ± 0.1 | 7.6 ± 0.4 | 7.4 ± 0.4 | 7.2 ± 0.2 |
| PLASMA SODIUM (mEq/L) | | | | |
| LR | 148 ± 1 | 149 ± 1 | 150 ± 1 | 148 ± 1 |
| DPDCLHb | 150 ± 1 | 145 ± 1 | 143 ± 1 | 143 ± 2 |
| PLASMA POTASSIUM (mEq/L) | | | | |
| LR | 4.0 ± 0.1 | 3.8 ± 0.1 | 3.6 ± 0.1 | 3.8 ± 0.2 |
| DPDCLHb | 4.5 ± 0.1 | 3.6 ± 0.1 | 4.1 ± 0.4 | 3.7 ± 0.2 |

Results shown in the Tables are reported as means ± SEM of 6 rats, except for period #6 of the DPDCLHb group in which n = 5.

The increase in plasma total protein concentration in the polyether oxirane polymerized hemoglobin solution group reflects the infusion and retention of the hemoglobin product (determined by the absence of bright red urine color).

Table 10 depicts the values for blood gases, MAP, and hematocrit.

TABLE 10

Effects of Polymerized Hemoglobin Solution on Blood Gas Values, MAP, and Hematocrit

| Period | 1 | 2 | 3 | 4 |
|---|---|---|---|---|
| BLOOD pH | | | | |
| LR | 7.31 ± 0.06 | 7.46 ± 0.03 | 7.46 ± 0.03 | 7.45 ± 0.04 |
| DPDCLHb | 7.31 ± 0.04 | 7.44 ± 0.02 | 7.45 ± 0.02 | 7.46 ± 0.03 |
| BLOOD pCO$_2$ | | | | |
| LR | 53.0 ± 7.1 | 45.8 ± 4.6 | 43.5 ± 4.2 | 41.4 ± 3.8 |
| DPDCLHb | 55.9 ± 6.8 | 51.3 ± 5.1 | 52.3 ± 6.5 | 50.0 ± 6.3 |
| BLOOD HCO$_3$ (mM) | | | | |
| LR | 26.1 ± 0.7 | 26.1 ± 0.5 | 25.6 ± 1.1 | 24.7 ± 1.2 |
| DPDCLHb | 27.5 ± 1.1 | 28.6 ± 2.2 | 23.4 ± 5.5 | 29.0 ± 2.2 |
| HEMATOCRIT (%) | | | | |
| LR | 40.2 ± 1.0 | 27.9 ± 1.0 | 31.7 ± 0.8 | 32.2 ± 0.7 |
| DPDCLHb | 38.8 ± 1.0 | 32.3 ± 0.9 | 28.0 ± 3.2 | 32.6 ± 0.7 |
| MAP (mmHg) | | | | |
| LR | 99 ± 10 | 82 ± 5 | 96 ± 8 | 92 ± 6 |
| DPDCLHb | 109 ± 9 | 119 ± 13 | 111 ± 11 | 113 ± 11 |

Results shown in the Tables are reported as means±SEM of 6 rats, except for period #6 of the DPDCLHb group in which n=5.

Hematocrit tended to decrease during the infusion of test and control articles, and then increase toward basal levels following cessation of the infusion. Both groups of rats were initially slightly acidotic during the basal period, but blood pH returned to normal in subsequent periods. The kidney, liver, lung, and heart tissues were evaluated for histopathology. The histopathology observed in the renal tissue was not associated with any measurable dysfunction.

Although the invention has been shown in connection with certain specific embodiments, it will be readily apparent to those skilled in the art that various changes in form and arrangement of steps can be made to suit requirements without departing from the spirit and scope of the invention.

What is claimed is:

1. A hemoglobin based composition comprising
   (a) hemoglobin monomers comprised of stroma-free aggregates of four globin chains, said monomers having been intramolecularly crosslinked and reacted with an oxirane to increase the average molecular weight of said monomers to at least about 120,000 Da;
   (b) oligomers of said hemoglobin monomers;
   (c) high molecular weight polymers of said hemoglobin based monomers; and
   (d) said composition having a P$_{50}$ of at least that of hemoglobin in human red cells.

2. A hemoglobin based composition comprising
   (a) hemoglobin monomers comprised of stroma-free aggregates of four globin chains, said monomers having been intramolecularly alpha-alpha crosslinked with diaspirin and reacted with an oxirane to increase the average molecular weight of said monomers to at least about 120,000 Da;
   (b) oligomers of said hemoglobin monomers;
   (c) high molecular weight polymers of said hemoglobin based monomers; and
   (d) said composition having a P$_{50}$ of at least that of hemoglobin in human red cells.

3. A hemoglobin based composition comprising
   (a) hemoglobin monomers comprised of stroma-free aggregates of four globin chains, said monomers having been intramolecularly alpha-alpha crosslinked with diaspirin and reacted with a long chain polyether oxirane having from about 15 to about 75 atoms in the chain to increase the average molecular weight of said monomers to at least about 120,000 Da;
   (b) oligomers of said hemoglobin monomers;
   (c) high molecular weight polymers of said hemoglobin based monomers; and
   (d) said composition having a P$_{50}$ of at least that of hemoglobin in human red cells.

* * * * *